(12) United States Patent
Soundararajan et al.

(10) Patent No.: US 9,308,569 B2
(45) Date of Patent: Apr. 12, 2016

(54) DEVICES AND METHODS FOR CRIMPING AND LOADING A MEDICAL DEVICE INTO A DELIVERY SYSTEM

(71) Applicant: Medtronic, Inc., Minneapolis, MN (US)

(72) Inventors: Gopikrishnan Soundararajan, Irvine, CA (US); Christopher Webster, Tustin, CA (US); Kenny Dang, Santa Ana, CA (US); Hussain Rangwala, Santa Ana, CA (US)

(73) Assignee: Medtronic, Inc., Minneapolis, MN (US)

( * ) Notice: Subject to any disclaimer, the term of this patent is extended or adjusted under 35 U.S.C. 154(b) by 420 days.

(21) Appl. No.: 13/757,327

(22) Filed: Feb. 1, 2013

(65) Prior Publication Data

US 2014/0215790 A1   Aug. 7, 2014

(51) Int. Cl.
*B21D 51/16* (2006.01)
*A61F 2/95* (2013.01)
*A61F 2/24* (2006.01)

(52) U.S. Cl.
CPC . *B21D 51/16* (2013.01); *A61F 2/95* (2013.01); *A61F 2/24* (2013.01); *A61F 2002/9522* (2013.01); *A61F 2250/001* (2013.01); *A61F 2250/006* (2013.01); *A61F 2250/0065* (2013.01); *Y10T 29/49826* (2015.01); *Y10T 29/5191* (2015.01)

(58) Field of Classification Search
CPC ............ A61F 2002/9522; B21D 51/16; Y10T 29/49913
See application file for complete search history.

(56) References Cited

U.S. PATENT DOCUMENTS

| | | |
|---|---|---|
| 1,580,416 A | 4/1926 | Pattison et al. |
| 1,927,528 A | 9/1993 | Nilsson |
| 5,611,587 A | 3/1997 | Brown |
| 5,626,604 A | 5/1997 | Cottone, Jr. |
| 5,672,169 A | 9/1997 | Verbeek |
| 5,931,851 A | 8/1999 | Morales |
| 5,951,540 A | 9/1999 | Verbeek |
| 5,992,000 A | 11/1999 | Humphrey et al. |
| 6,009,614 A | 1/2000 | Morales |
| 6,018,857 A | 2/2000 | Duffy et al. |
| 6,024,737 A | 2/2000 | Morales |
| 6,051,002 A | 4/2000 | Morales |
| 6,063,092 A | 5/2000 | Shin |
| 6,063,102 A | 5/2000 | Morales |
| 6,360,577 B2 * | 3/2002 | Austin ............................ 29/237 |

(Continued)

OTHER PUBLICATIONS

PCT/US2014/014092, PCT Search Report and Written Opinion, mailed May 15, 2014.

*Primary Examiner* — Christopher M Koehler (57) ABSTRACT

A device for crimping an expandable medical device and loading the expandable medical device into a delivery system includes an actuator, a compression assembly, and a pusher. The compression assembly is disposed in a compression chamber of the actuator and includes a plurality of compression elements coupled to each other to form a central cavity. The compression elements are coupled to the actuator such that rotation of the actuator causes the compression elements to rotate such that the central cavity radially compresses from an expanded configuration to a compressed configuration. The pusher includes a pusher rod and is configured to translate relative to the actuator towards the compression chamber when the cavity is in the compressed configuration such that the pusher rod may enter the cavity and push the medical device out of the cavity into delivery system.

20 Claims, 7 Drawing Sheets

(56) References Cited

U.S. PATENT DOCUMENTS

| | | |
|---|---|---|
| 6,609,283 B1 | 8/2003 | Somerville |
| 6,629,350 B2 | 10/2003 | Motsenbocker |
| 6,730,118 B2 | 5/2004 | Spenser et al. |
| 6,925,847 B2 | 8/2005 | Motsenbocker |
| 6,983,522 B2 | 1/2006 | Weller et al. |
| 7,117,573 B1 | 10/2006 | Hu |
| 7,334,798 B2 | 2/2008 | Haliburton |
| 7,530,253 B2 | 5/2009 | Spenser et al. |
| 8,978,221 B1 | 3/2015 | Somerville et al. |
| 2002/0138966 A1* | 10/2002 | Motsenbocker ........ A61F 2/958 29/516 |
| 2003/0070682 A1 | 4/2003 | Wilson et al. |
| 2003/0135970 A1* | 7/2003 | Thornton ................ A61F 2/958 29/270 |
| 2003/0225445 A1 | 12/2003 | Derus et al. |
| 2004/0128818 A1* | 7/2004 | Motsenbocker .......... A61F 2/95 29/505 |
| 2004/0148007 A1 | 7/2004 | Jackson et al. |
| 2006/0004469 A1* | 1/2006 | Sokel .................... A61F 2/2415 29/516 |
| 2007/0056346 A1* | 3/2007 | Spenser ................ A61F 2/2412 72/402 |
| 2007/0239271 A1 | 10/2007 | Nguyen |
| 2008/0058916 A1 | 3/2008 | Huang et al. |
| 2008/0071362 A1 | 3/2008 | Tuval et al. |
| 2009/0018570 A1 | 1/2009 | Righini et al. |
| 2009/0093876 A1* | 4/2009 | Nitzan .................. A61F 2/2433 623/2.11 |
| 2010/0036484 A1 | 2/2010 | Hariton et al. |
| 2010/0292779 A1* | 11/2010 | Straubinger .......... A61F 2/2427 623/1.23 |
| 2010/0292780 A1 | 11/2010 | Straubinger et al. |
| 2012/0101569 A1 | 4/2012 | Mearns et al. |
| 2014/0215791 A1 | 8/2014 | Soundararajan et al. |
| 2015/0101635 A1 | 4/2015 | Schnol |

* cited by examiner

DEVICES AND METHODS FOR CRIMPING AND LOADING A MEDICAL DEVICE INTO A DELIVERY SYSTEM

BACKGROUND

1. Field

The present invention can relate to devices and methods for crimping and loading a medical device into a delivery system.

2. Background

Recently, minimally invasive approaches have been developed to facilitate surgical and catheter-based implantation of prostheses. For example, during transcatheter medical device implantations, a medical device such as a stented device is radially contracted or crimped to a diameter smaller than the diameter of the device when implanted. The crimped medical device is then loaded onto a delivery system such as a delivery catheter so that the medical device can be introduced into a body lumen, for example, into the femoral artery, the subclavian artery, or the aorta, or into a body cavity, for example, a chamber of the heart (e.g., the ventricle). Using the delivery catheter, the medical device can be guided to a desired implantation site through the body lumen or body cavity and deployed at the desired site. Current methods for crimping and loading the medical device can be tedious and can potentially damage the medical device.

Accordingly, improved systems for crimping and loading a medical device for use in such delivery systems are desired.

BRIEF SUMMARY

In some embodiments, a device for crimping and loading an expandable medical device from an expanded configuration to a compressed configuration includes an actuator, a compression assembly, and a pusher. The actuator may include a compression chamber and an opening. The compression assembly may be disposed in the compression chamber and may include a plurality of compression elements. The compression elements may be coupled to each other to form a central cavity. The compression elements may also be coupled to the actuator such that rotation of the actuator causes the compression elements to rotate such that the central cavity radially compresses from an expanded configuration to a compressed configuration. The pusher may include a pusher rod configured to push the radially compressed medical device out of the central cavity when in the compressed configuration. The pusher may be coupled to the actuator and be configured to translate relative to the actuator towards the compression chamber when the cavity is in the compressed configuration such that the pusher rod may enter the cavity and push the medical device out of the cavity into delivery system.

BRIEF DESCRIPTION OF THE FIGURES

The accompanying figures, which are incorporated herein, form part of the specification and illustrate embodiments of the invention. Together with the description, the figures further serve to explain the principles of and to enable a person skilled in the relevant art(s) to make and use the devices and methods described herein.

DETAILED DESCRIPTION

The following detailed description of devices and methods for crimping and loading a medical device into a delivery system refers to the accompanying figures that illustrate certain embodiments. Other embodiments are possible. Modifications can be made to the embodiments described herein without departing from the spirit and scope of the present invention. Therefore, the following detailed description is not meant to be limiting. Further, it would be apparent to one of skill in the art that the devices and methods described below can be implemented in many different embodiments of hardware. Any actual hardware described is not meant to be limiting. The operation and behavior of the devices and methods presented are described with the understanding that modifications and variations of the embodiments are possible.

Figure 1:
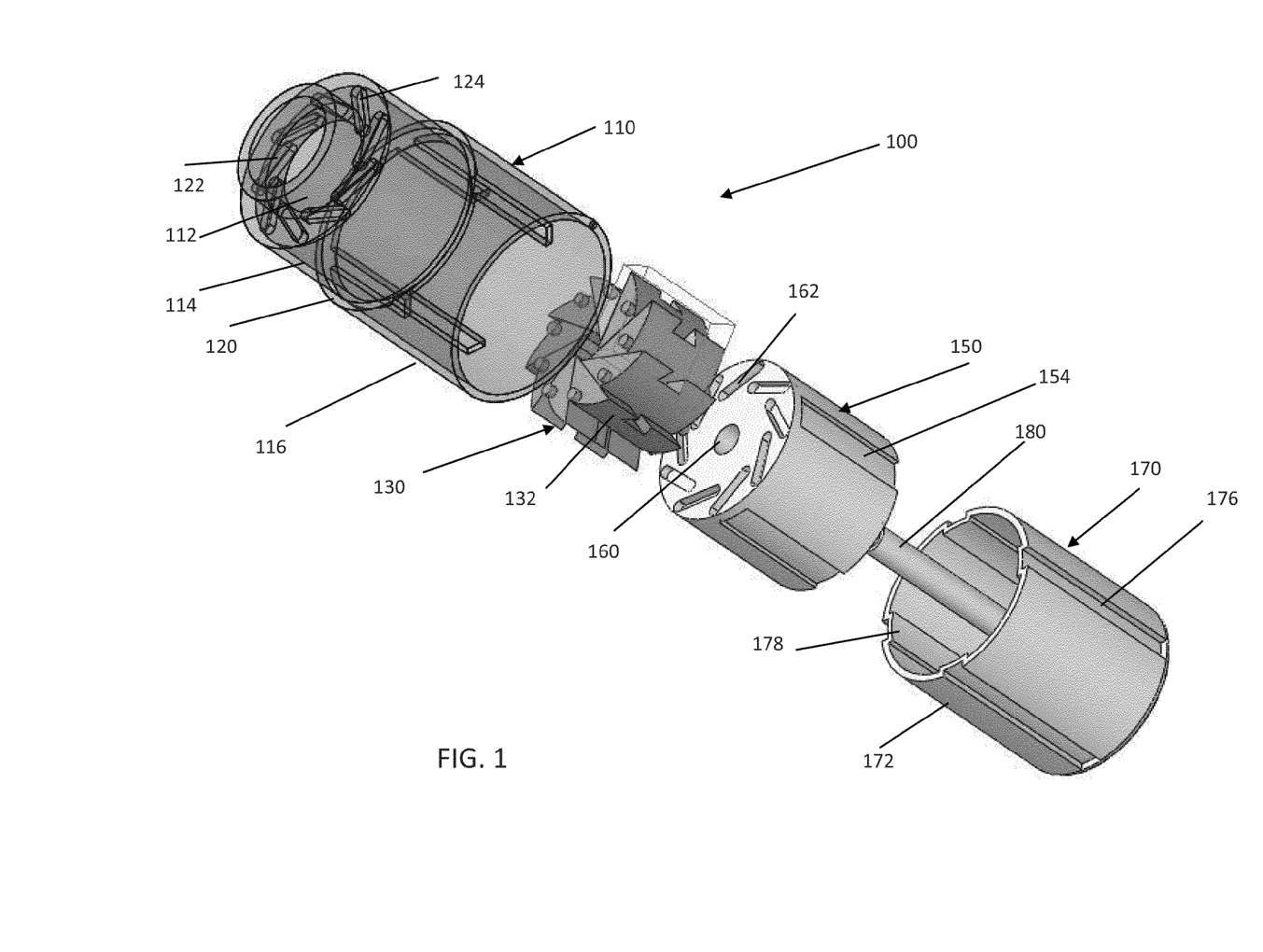
FIG. 1 illustrates an exploded perspective view of a crimping and loading device.

FIG. 1 illustrates an exploded view of a crimping and loading device 100 according to an embodiment hereof. Device 100 includes an actuator 110, a compression assembly 130, an inner sleeve 150, and a pusher 170. The individual parts will be described below and then the assembly and operation thereof.

Figure 2:
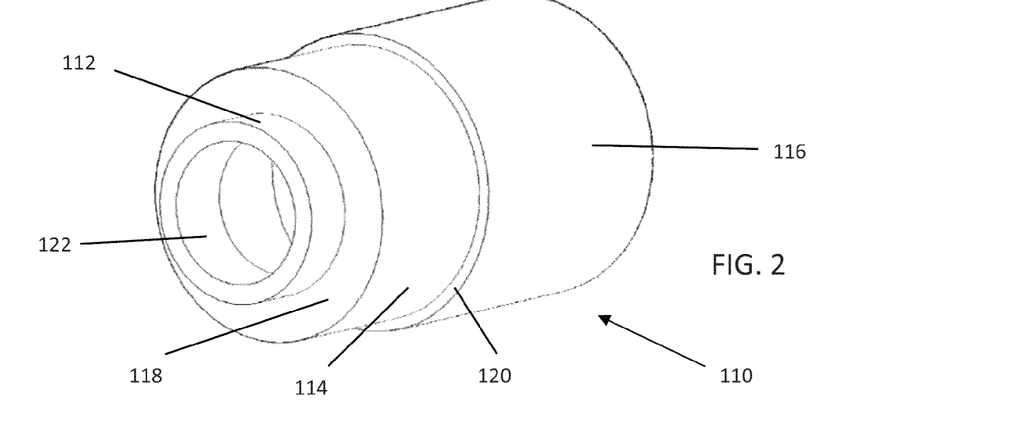
FIG. 2 illustrates a front perspective view of the outer cylinder of the crimping and loading device of FIG. 1.
Figure 3:
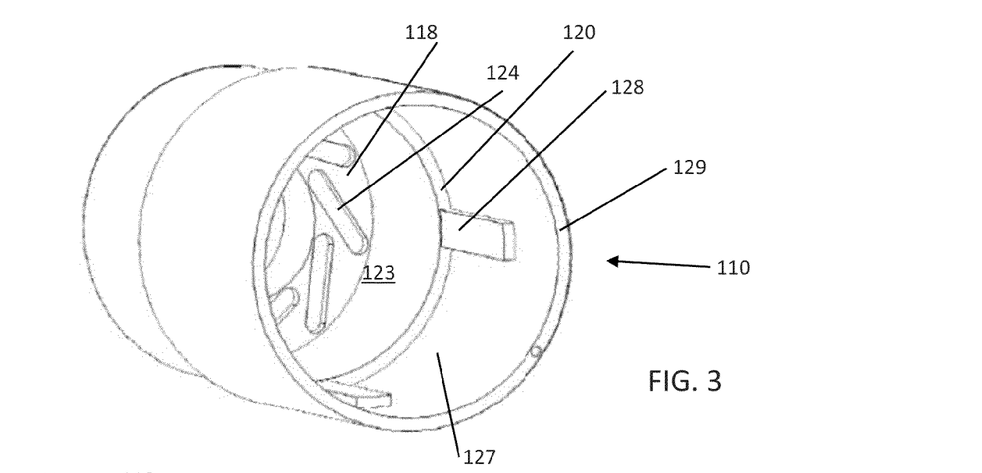
FIG. 3 illustrates a rear perspective view of the outer cylinder of FIG. 2.
Figure 4:
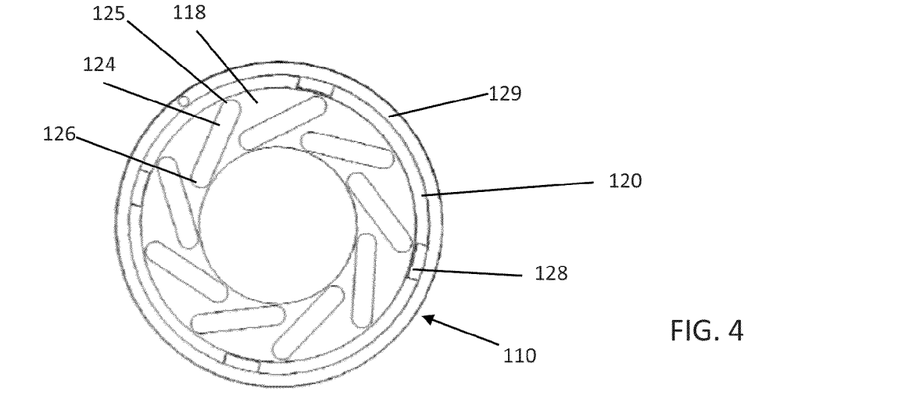
FIG. 4 illustrates a rear view of the outer cylinder of FIG. 2.

FIGS. 2-4 show various views of actuator 110 of crimping and loading device 100. Actuator 110 is generally an open cylinder but includes step-downs, shoulders or transitions in its diameter to accommodate other parts of crimping and loading device 100. In particular, actuator 110 includes a first or insertion section 112, a second or compression section 114, and a third o receiving section 116. In the embodiment shown, insertion section 112 has a smaller diameter than compression section 114, which has a smaller diameter than third section 116. Further, a shoulder 118 is formed at mating edges of insertion section 112 and a compression section 114. Another shoulder 120 is formed at mating edges of compression section 114 and third section 116. As described above, actuator 110 is an open cylinder with transitions in diameter. Accordingly, an opening 122 is provided through insertion section 118. Opening 122 is sized to accommodate a medical device (described below) with the medical device in its radially expanded configuration.

Compression section 114 includes a chamber 123 defined between an inner surface of shoulder 118 and shoulder 120, as shown in FIG. 3. Chamber 123 is sized to accommodate compression assembly 130, as described in more detail below. Further, the inner surface of shoulder 118 includes a plurality of slots or grooves 124. In the embodiment shown, there are nine grooves 124 to accommodate the compression elements of compression assembly 130, as described in more detail below. Each groove 124 is pill shaped and includes a first end 125 disposed adjacent an outer edge of shoulder 118 and a second end 126 disposed adjacent an inner edge of shoulder 118, as best seen in FIGS. 3 and 4. Further, each groove 124 is angled with respect to the radial and longitudinal axes of actuator 110, as shown in FIG. 4. In the embodiment shown, each groove 124 extends in a counter-clockwise direction from first end 125 to second end 126 (clockwise from second end 126 to first end 125). However, those skilled in the art would recognize that other patterns may be utilized.

Receiving or third section 116 includes an edge 129 which defines an end of the actuator 110. Section 116 further includes an inner surface 127 with a plurality of projections or protrusions 128 extended radially inward from inner surface 129 cylindrical. Protrusions 128 also extend from shoulder 120 towards edge 129, as shown in FIG. 3. In the embodiment shown, actuator 110 includes four protrusions 128. However, those skilled in the art would recognize that more or less protrusions may be utilized depending on the relative sizes of the parts, the size of the medical device, the degree of rotation required to radially compress the compression assembly, design choices, and other factors known to those skilled in the art. Protrusions 128 are sized and shaped to fit within and slide within grooves on an outer surface of pusher 170, as described in more detail below.

Figure 5:
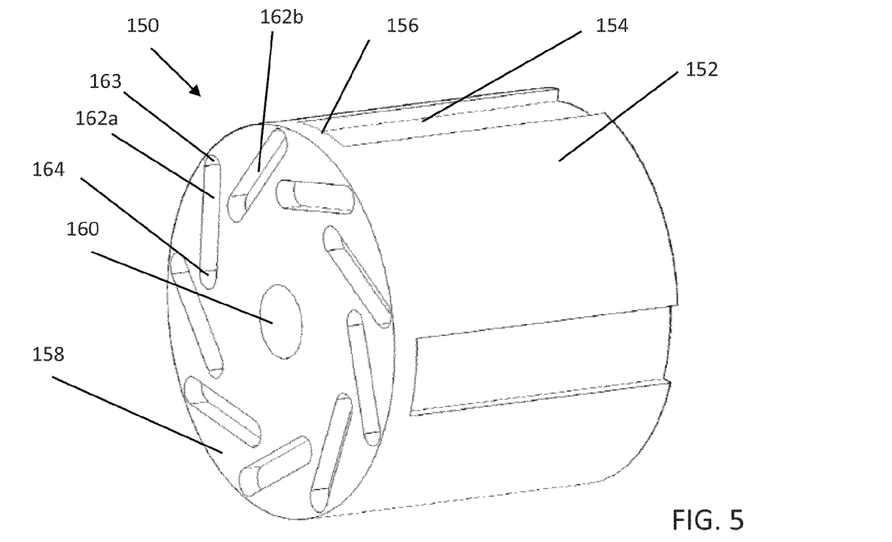
FIG. 5 illustrates a front perspective view of the inner sleeve of the crimping and loading device of FIG. 1.
Figure 6:
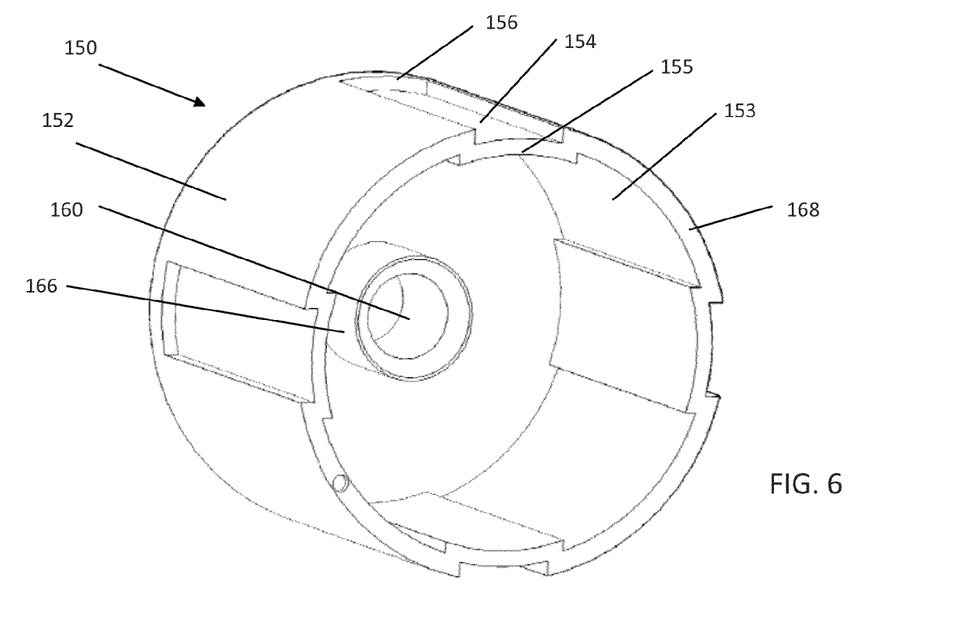
FIG. 6 illustrates a rear perspective view of the inner sleeve of FIG. 5.

Inner sleeve 150 is illustrated in FIGS. 5 and 6. In the embodiment shown, inner sleeve 150 is generally an open cylinder in shape and includes a wall or surface 158 at one end thereof. Sleeve 150 includes an outer surface 152 and an inner surface 153. Sleeve 150 further includes notches or grooves 154 in outer surface 152 and corresponding protrusions 155 extending from inner surface 153, as shown in FIG. 6. In the embodiment shown, there are four grooves 154 and corresponding protrusions 155. However, those skilled in the art would recognize that more or less grooves and protrusion may be utilized. Grooves 154 are sized and shaped to receive protrusions 178 of pusher, described in more detail below. It would be understood by those skilled in the art that protrusions 155 are not required. In other words, grooves 154 in outer surface 152 without corresponding protrusions 155 may be utilized. Grooves 154 of inner sleeve extend from a shoulder 156 adjacent a first end of sleeve 150 to a second end 168 of sleeve 150.

At the first end of sleeve 150 is an end wall 158. Wall 158 is generally perpendicular to the longitudinal axis of sleeve 150 and includes an opening 160 therethrough. Opening 160 is generally circular in shape and is sized and shaped to accommodate post 180 of pusher 170, as described in more detail below. An extension 166, as shown in FIG. 6, may extend from an inner surface of wall 158 to extend opening 160 towards second end 168. An outer surface of wall 158 includes a plurality of slots or grooves 162. In the embodiment shown, there are nine grooves 162 to accommodate the compression elements of compression assembly 130, as described in more detail below. Each groove may be labeled as groove 162 or may be labeled with letter suffixes, i.e., 162a, 162b ... 162x, depending on the number of grooves 162. Each groove 162 is pill shaped and includes a first end 163 disposed adjacent an outer edge of shoulder wall 158 and a second end 164 disposed closer to opening 160, as best seen in FIGS. 5 and 6. Further, each groove 162 is angled with respect to the radial and longitudinal axes of sleeve 110. In the embodiment shown, each groove 162 extends in a counter-clockwise direction from first end 163 to second end 164 (clockwise from second end 164 to first end 163). However, those skilled in the art would recognize that other patterns may be utilized.

Figure 7:
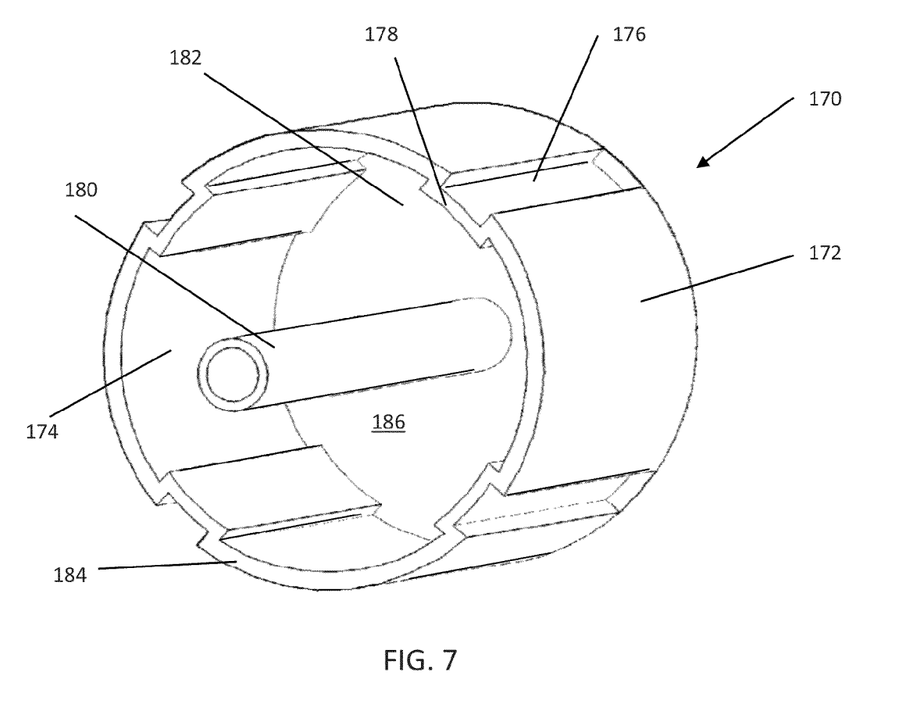
FIG. 7 illustrates a front perspective view of the pusher of the crimping and loading device of FIG. 1.

FIG. 7 illustrates an embodiment of pusher 170. Pusher 170 is generally an open cylinder in shape with a wall 180 disposed at one end thereof. The cylindrical surface of pusher 170 includes an outer surface 172 and an inner surface 174. A plurality of grooves 176 are disposed in outer surface 172 and corresponding protrusions 178 extend from inner surface 174. Grooves 176 are sized and shaped to received protrusions 128 of actuator 110 and protrusions 178 are sized and shaped to fit within grooves 154 of sleeve 150. A rod 180 extends from wall 182 towards a second end of pusher 180 defined by edge 184. Rod 180 extends generally along the longitudinal axis of pusher 170 and is sized and shaped to be received within opening 160 of sleeve 150, as described in more detail below. Pusher 170 defines an inner chamber 186 sized and shaped to receive sleeve 150 therein.

Compression assembly 130 is illustrated in FIG. 1. In the present embodiment, compression assembly 130 includes nine compression elements 132 arranged in a circular pattern adjacent to each other. However, those skilled in the art would recognize that more or less compression elements may be utilized. FIG. 3 shows three of the compression elements 132, labeled as compression elements 132a, 132b, and 132c. Each compression element 132 is similar to a triangular prism with a curved surface 149 and other modifications as will be discussed in detail. However, those skilled in the art would recognize that other shapes may be utilized.

Figure 8:
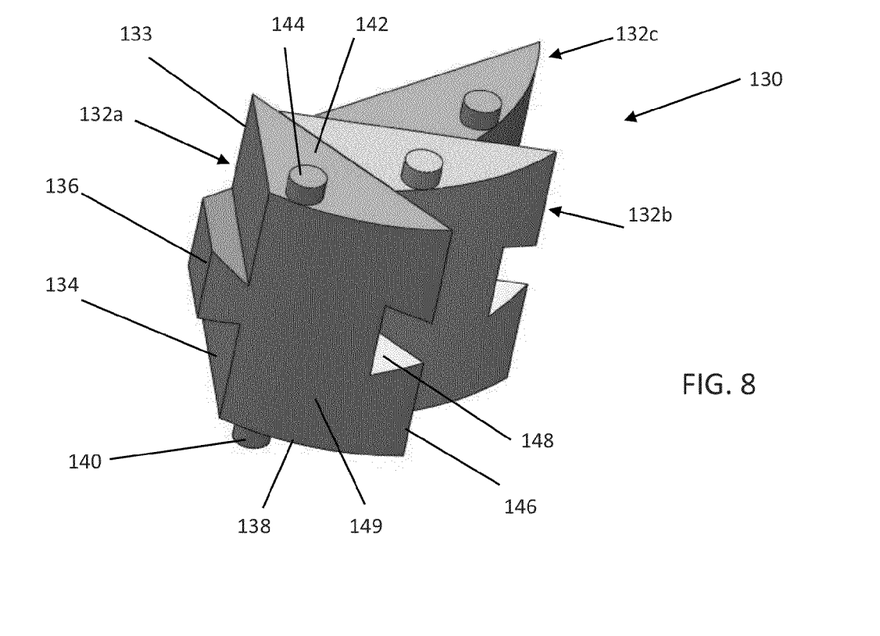
FIG. 8 illustrates three compression elements of the compression assembly of the crimping and loading device of FIG. 1.

Compression element 132a shown in FIG. 3 will be described in detail. The other compression elements 132 are identical to compression element 132a. Compression element 132 includes an apex 133 where a first surface or plane 134 and a second surface or plane 146 meet. Opposite apex 133 is a base or third surface 149. Base surface in 149 in the present embodiment is curved such that when the compression assembly 130 is located in compression chamber 123 of actuator 110, the base surfaces 149 of the compression elements 132 are shaped generally circularly to match an inside surface of actuator 110. First surface 134 includes a protrusion 136 extending therefrom. Second surface 146 includes a groove 148 disposed therein. Groove 148 is sized and shaped to receive the protrusion 136 of the adjacent compression element 132b, as shown in FIG. 8. Each compression element 132 first includes fourth and fifth surfaces 138, 142, wherein the edges of fourth and fifth surface are shared with the edges of first, second and third surfaces 134, 146, 148. Extending from fourth surface 138 is a post 140 and extending from fifth surface 142 is a post 144. Posts 140. 144 are sized and shaped to fit into grooves 124 and 162.

Figure 12:
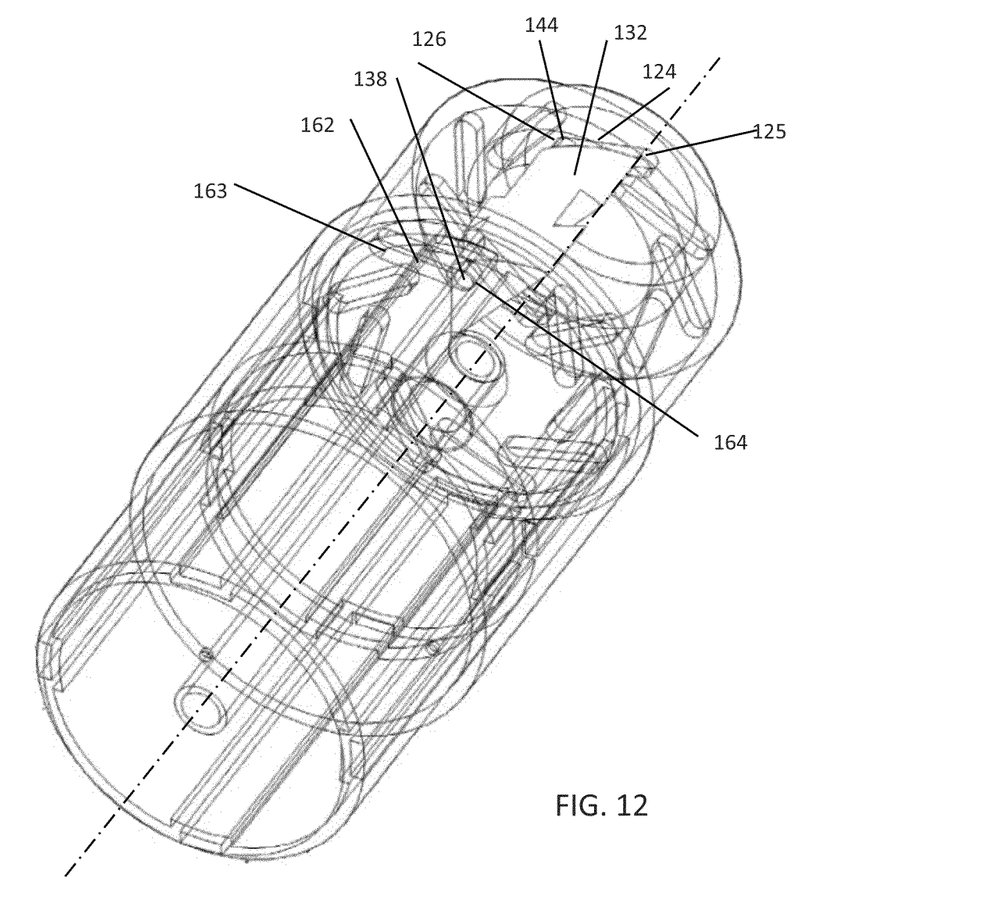
FIG. 12 illustrates a perspective view of the crimping and loading device with only one of the compression elements shown and in the compressed configuration, with parts of the device shown transparent.

With compression elements 132 joined together in a circular pattern to form a cylinder, apexes 133 are located in the direction of the center or longitudinal axis of the cylinder. Due to the size and shape of the compression elements, a cavity 190 is formed by the compression elements 132, as shown in FIG. 12. The size of the cavity may be changed due to the ability of each protrusion 136 to slide with the groove 148 of the adjacent compression element. Thus, cavity 190 can change from an expanded or first diameter to a compressed or second diameter, wherein the first diameter is larger than the second diameter. FIG. 12 shows cavity 190 in the second or compressed diameter.

Figure 9:
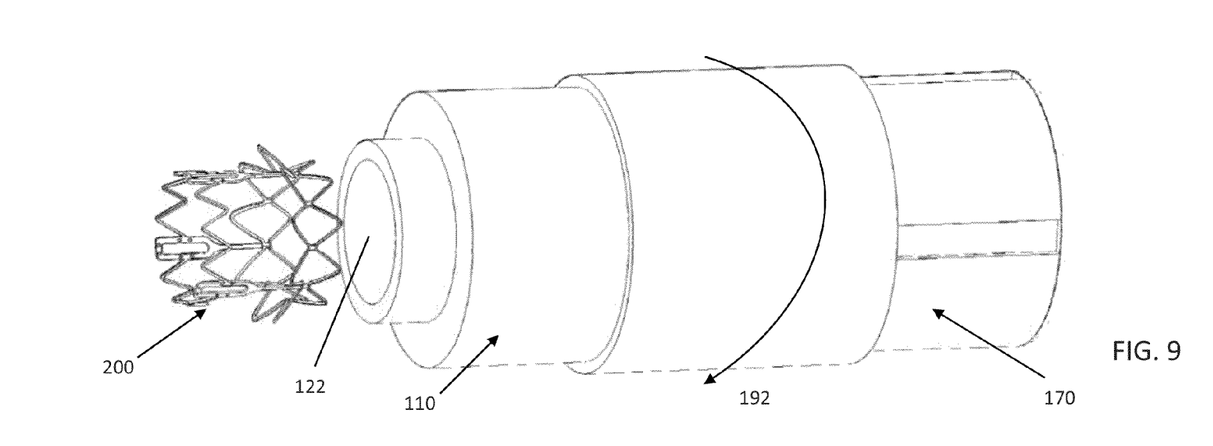
FIG. 9 illustrates perspective view of the crimping and loading device.

Operation of crimping and loading device 100 will now be described with respect to FIGS. 9-12. FIG. 9 shows crimping and loading device 100 prepared to receive medical device 200. Medical device 200 can be, for example, a fully compressible or partially compressible medical device. In some embodiments, medical device 200 can be configured to be introduced into one or more body lumens or body cavities, such as for example a femoral artery, a subclavian artery, an aorta, a chamber of the heart, and/or a ventricle. In some embodiments, medical device 200 can be in the form of a compressible stent or frame for use in surgical, trans-catheter, and/or trans-apical heart valve procedures. Medical device 200 can include, for example, a compressible prosthetic heart valve attached to a compressible frame. In some embodiments, medical device 200 can be any other suitable device for use in trans-catheter procedures, such as for example embolic filters or embolic filter retrievers.

Crimping and loading device 100 is assembled as shown in FIG. 1. In particular, compression assembly 130 is disposed within compression chamber 123 of actuator 110 with post 144 of each compression element 132 disposed in a respective groove 124 of actuator 110. Inner sleeve 150 is disposed within actuator 110 with post 138 of each compression element disposed in a respective groove 162 of sleeve 150. Further, pusher 170 is disposed around inner sleeve 150 with protrusions 178 of pusher 170 aligned with grooves 154 of inner sleeve 150 and rod 180 of pusher 170 inserted into opening 160 of sleeve 150. Pusher 170 is inserted into actuator 110.

With crimping and loading device 100 assembled, medical device 200 is inserted into opening 122 of actuator 110 and disposed within cavity 190 formed by compression elements 132. Although not shown in FIG. 9, compression elements 132 are arranged such that post 144 of each compression element is at first end 125 of groove 124 of actuator 110 and post 138 is disposed at first end 163 of groove 162 of inner sleeve 150. In such positions, posts 144, 138 are disposed at the outer diameter of surface 118 and wall 158, respectively. Accordingly, cavity 190 is at its first or expanded diameter such that medical device 200 can be disposed therein. In the expanded configuration, protrusions 178 of pusher 170 are aligned with grooves 154 of inner sleeve 154. However, protrusions 128 of actuator 110 are not aligned with grooves 176 of pusher 170. Accordingly, edge 184 of pusher 170 abuts against protrusions 128 of actuator 110, preventing rod 180 of pusher from extending beyond wall 158 of inner sleeve 150.

Figure 10:
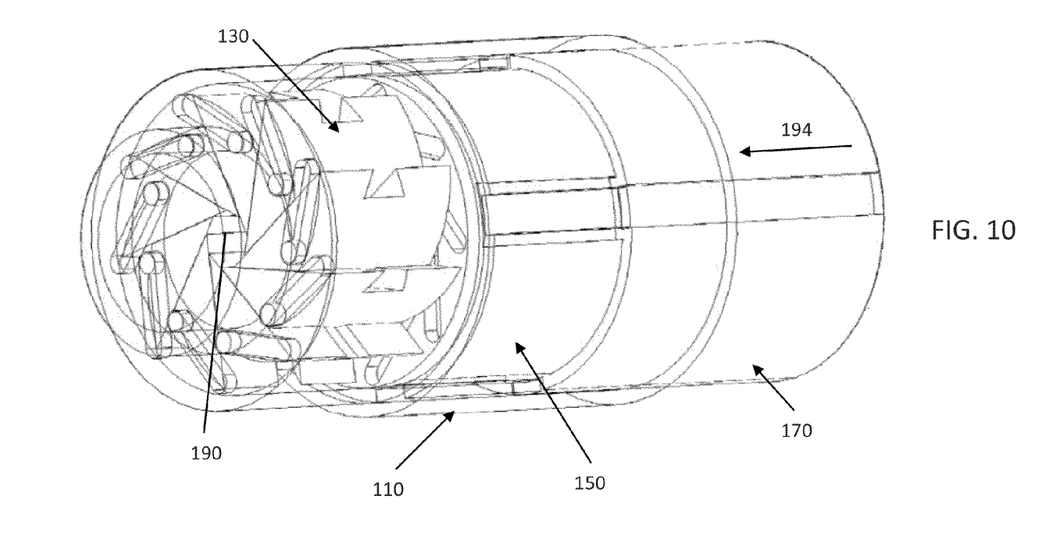
FIG. 10 illustrates a perspective view of the crimping and loading device with the compression assembly in the compressed configuration and parts of the device shown transparent.
Figure 11:
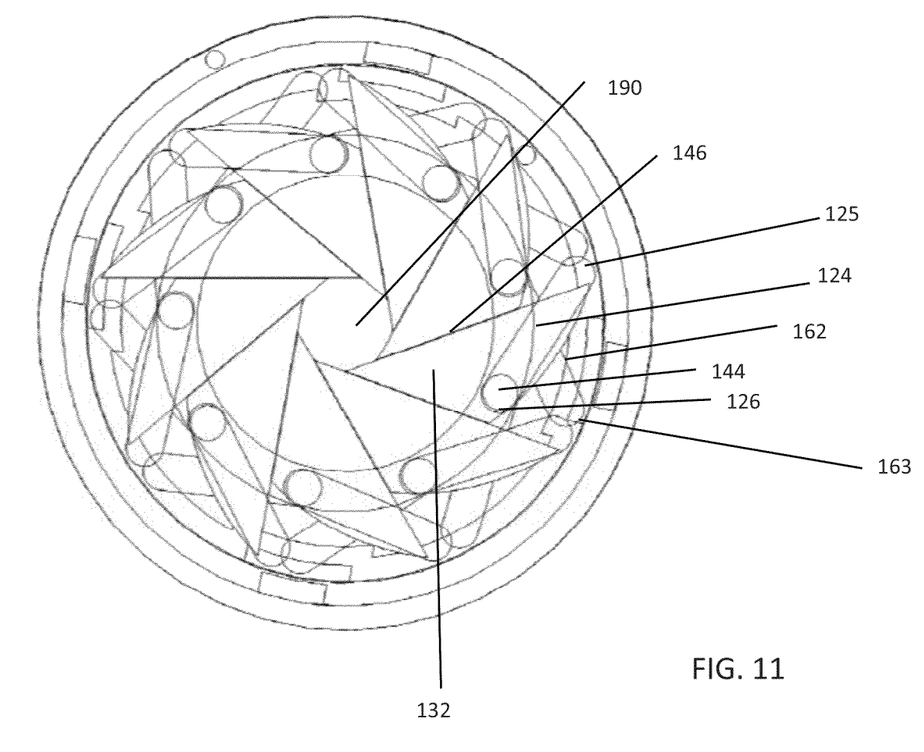
FIG. 11 illustrates a front view of the crimping and loading device with the compression assembly in the compressed configuration and parts of the device shown transparent.

With medical device 200 disposed in cavity 190 of compression assembly 130, actuator 110 is rotated as shown by arrow 192 in FIG. 9 while pusher 170 and inner sleeve 150 coupled thereto are held stationary or rotated in the opposite direction of actuator 110. As actuator 110 is rotated relative to sleeve 150, pin 144 slides within groove 124 and pin 138 slides within groove 162 until second end 126 of groove 124 contacts pin 144 and second end 164 of groove 162 contacts pin 138. The movement of the grooves/pins causes compression elements 132 to rotate such that second surface 146 of each compression element 132 is at a steeper angle relative to the longitudinal axis of device 100 in the compressed configuration as compared to the expanded configuration. This rotation causes edge 133 of each compression element 132 to move closer to the longitudinal axis of the device 100, thereby reducing the diameter of cavity 190. This compressed configuration of crimping and loading device 100 is shown in FIGS. 10-12 with all parts except the compression elements 132 shown transparent and with only one compression element 132 shown in FIG. 12. As can be seen in FIGS. 10 and 11, cavity 190 formed by compression elements 132 is in its reduced diameter configuration. The compression of cavity 190 from its expanded configuration to its compressed configuration also compresses medical device 200 (not shown in FIGS. 10-12) disposed within cavity 190 from its expanded configuration to its compressed or reduced diameter configuration.

When actuator 110 is rotated such that pins 144, 138 of compression elements 132 contact second end 126, 164 of grooves 124, 162, protrusions 128 on inner surface 127 of actuator 110 become aligned with grooves 176 on outer surface 172 of pusher 170. With protrusions 178 of inner surface 174 of pusher 170 aligned with grooves 154 on outer surface of inner sleeve 150, the alignment of protrusions 128 with grooves 176 allows pusher 170 to be pushed towards opening 122 of actuator 110. A delivery catheter or other device onto which medical device 200 is to be loaded can be aligned with cavity 190 of compression assembly 130. In some embodiments, a portion of actuator 110, such as insertion section 112, can include a fixture (not shown) that attaches to the delivery system. Thus, as pusher 170 is translated towards opening 122, as shown by arrow 194 in FIG. 10, rod 180 extends through opening 160 in wall 158 of sleeve 150 and contacts medical device 200. Continued translation of pusher 170 causes rod 180 to push medical device 200 out of cavity 190 and onto the delivery system or other device (not shown). Thus, device 100 can be configured to crimp and load the medical device without requiring manual repositioning of the medical device following the crimping operation.

The choice of materials for the parts of crimping and loading device 100 can be informed by the requirements of mechanical properties, temperature sensitivity, biocompatibility, moldability properties, or any other factor apparent to a person having ordinary skill in the art. For example, one or more of the parts (or a portion of one of the parts) can be made from suitable plastics, such as suitable thermoplastics, suitable metals, and/or other suitable materials.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

We claim:

1. A device for crimping and loading an expandable medical device from an expanded configuration to a compressed configuration, the device comprising:

an actuator including a compression chamber and an opening;

a compression assembly disposed in the compression chamber, wherein the compression assembly includes a plurality of compression elements arranged adjacent each other and forming a central cavity therein, wherein the compression elements are coupled to the actuator such that rotation of the actuator causes the compression elements to rotate such that the central cavity radially compresses from an expanded configuration to a compressed configuration;

a pusher coupled to the actuator opposite the opening, wherein the pusher includes an outer wall defining a cavity and a pusher rod disposed within the cavity, the pusher rod being sized and shaped generally similar to the central cavity formed by the compression elements in the compressed configuration, wherein the pusher is configured to translate relative to the actuator such that the pusher rod may enter the central cavity with the central cavity in the compressed configuration; and a sleeve disposed within the actuator opposite the opening, wherein the sleeve is also disposed within the cavity of the pusher.

2. The device of claim 1, wherein the opening is sized and shaped to receive the medical device with the medical device in the expanded configuration.

3. The device of claim 1, wherein the central cavity in the expanded configuration is sized and shaped to receive the medical device with the medical device in the expanded configuration.

4. The device of claim 1, wherein the actuator includes a shoulder between the opening and the compression chamber.

5. The device of claim 4, wherein an inner surface of the shoulder includes a plurality of grooves, wherein each groove includes a first end adjacent an outer edge of the shoulder and a second end disposed radially inward from the first end.

6. The device of claim 5, wherein each compression element includes a first rod sized and shaped to fit within one of the grooves of the inner surface of the shoulder.

7. The device of claim 6, wherein the sleeve includes a surface facing the compression chamber, and where the surface includes a plurality of grooves, wherein each groove includes a first end adjacent an outer edge of the surface and a second end disposed radially inward from the first end.

8. The device of claim 7, wherein each compression element includes a second rod sized and shaped to fit in one of the groves of the sleeve.

9. The device of claim 1, further comprising a sleeve disposed within the actuator and coupled to the compression elements.

10. The device of claim 9, wherein the sleeve is coupled to the pusher such that the pusher and sleeve do not rotate relative to each other, and wherein the pusher may translate relative to the sleeve.

11. The device of claim 10, wherein when the actuator and sleeve are disposed in a first position the compression assembly is in the expanded configuration and wherein when the actuator and sleeve are disposed in a second position the compression assembly is in the compressed configuration.

12. The device of claim 1, wherein the sleeve includes an opening disposed therethrough, wherein the opening through the sleeve is shaped and sized to received pusher rod therethrough.

13. A device for crimping and loading an expandable medical device from an expanded configuration to a compressed configuration, the device comprising:

an actuator including a compression chamber, an opening, and a shoulder between the opening and the compression chamber, wherein an inner surface of the shoulder includes a plurality of grooves, wherein each groove includes a first end adjacent an outer edge of the shoulder and a second end disposed radially inward from the first end;

a compression assembly disposed in the compression chamber, wherein the compression assembly includes a plurality of compression elements arranged adjacent each other and forming a central cavity therein, wherein the compression elements are coupled to the actuator such that rotation of the actuator causes the compression elements to rotate such that the central cavity radially compresses from an expanded configuration to a compressed configuration;

a pusher coupled to the actuator opposite the opening, wherein the pusher includes a pusher rod sized and shaped generally similar to the central cavity in the compressed configuration, wherein the pusher is configured to translate relative to the actuator such that the pusher rod may enter the central cavity with the central cavity in the compressed configuration; and a sleeve disposed within the actuator opposite the opening, wherein the sleeve is sized and shaped to fit within the pusher, wherein the sleeve includes a surface facing the compression chamber, and where the surface includes a plurality of grooves, wherein each groove includes a first end adjacent an outer edge of the surface and a second end disposed radially inward from the first end, wherein each compression element includes a first rod sized and shaped to fit within one of the grooves of the inner surface of the shoulder.

14. The device of claim 13, wherein each compression element includes a second rod sized and shaped to fit in one of the grooves of the sleeve.

15. The device of claim 14, wherein the compression elements are disposed between the shoulder of the actuator and the surface of the sleeve.

16. The device of claim 14, wherein the grooves on the inner surface of the shoulder and the grooves on the surface of the sleeve are angled with respect to a longitudinal axis of the device.

17. The device of claim 16, wherein in the expanded configuration of the compression assembly, each first rod of the compression elements is disposed in a respective groove of the shoulder adjacent the first end of the groove and each second rod of the compression elements is disposed in a respective groove of the sleeve adjacent the first end of the groove, and wherein in the compressed configuration of the compression assembly, each first rod of the compression elements is disposed in the respective groove of the shoulder adjacent the second end of the groove and each second rod of the compression elements is disposed in the respective groove of the sleeve adjacent the second end of the groove.

18. A device for crimping and loading an expandable medical device from an expanded configuration to a compressed configuration, the device comprising:

an actuator including a compression chamber and an opening;

a compression assembly disposed in the compression chamber, wherein the compression assembly includes a plurality of compression elements arranged adjacent each other and forming a central cavity therein, wherein the compression elements are disposed entirely between the first and second longitudinal ends of the actuator and are coupled to the actuator such that rotation of the actuator causes the compression elements to rotate such that the central cavity radially compresses from an expanded configuration to a compressed configuration;

a pusher coupled to the actuator opposite the opening, wherein the pusher includes a pusher rod sized and shaped generally similar to the central cavity in the compressed configuration, wherein the pusher is configured to translate relative to the actuator such that the pusher rod may enter the central cavity with the central cavity in the compressed configuration; and a sleeve disposed within the actuator and coupled to the compression elements, wherein the sleeve is coupled to the pusher such that the pusher and sleeve do not rotate relative to each other, and wherein the pusher may translate relative to the sleeve, and wherein protrusions on an inner surface of the pusher are coupled to grooves on an outer surface of the sleeve to couple the pusher and sleeve to each other.

19. A device for crimping and loading an expandable medical device from an expanded configuration to a compressed configuration, the device comprising:

an actuator including a compression chamber and an opening;

a compression assembly disposed in the compression chamber, wherein the compression assembly includes a plurality of compression elements arranged adjacent each other and forming a central cavity therein, wherein the compression elements are coupled to the actuator such that rotation of the actuator causes the compression elements to rotate such that the central cavity radially compresses from an expanded configuration to a compressed configuration;

a pusher coupled to the actuator opposite the opening, wherein the pusher includes a pusher rod sized and shaped generally similar to the central cavity in the compressed configuration, wherein the pusher is configured to translate relative to the actuator such that the pusher rod may enter the central cavity with the central cavity in the compressed configuration; and a sleeve disposed within the actuator and coupled to the compression elements, wherein the sleeve is coupled to the pusher such that the pusher and sleeve do not rotate relative to each other, and wherein the pusher may translate relative to the sleeve, wherein when the actuator and sleeve are disposed in a first position the compression assembly is in the expanded configuration and wherein when the actuator and sleeve are disposed in a second position the compression assembly is in the compressed configuration, and wherein in the first position, the pusher is prevented from translating towards the actuator such that the pusher rod does not extend into the cavity of the compression assembly, and wherein in the second position, the pusher can translate relative to the actuator and the sleeve such that the pusher rod can extend into the cavity of the compression assembly.

20. The device of claim 19, wherein in the first position, a plurality of protrusions extending from an inner surface of the actuator block the pusher from translating towards the compression chamber sufficiently to have the pusher rod extend into the cavity, and wherein in the second position, the protrusions extending from the inner surface of the actuator align with grooves in an outer surface of the pusher to permit the pusher to translate relative to the actuator such that the pusher rod can extend into the cavity.

* * * * *